US011827675B2

(12) United States Patent
Garg et al.

(10) Patent No.: US 11,827,675 B2
(45) Date of Patent: Nov. 28, 2023

(54) STABLE CELL LINE SECRETING CHIKUNGUNYA VIRUS (CHIKV) VIRUS LIKE PARTICLES (VLP) FOR VACCINES

(71) Applicant: Texas Tech University System, Lubbock, TX (US)

(72) Inventors: Himanshu Garg, El Paso, TX (US); Anjali Joshi, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 333 days.

(21) Appl. No.: 17/268,573

(22) PCT Filed: Sep. 26, 2019

(86) PCT No.: PCT/US2019/053049
§ 371 (c)(1),
(2) Date: Feb. 15, 2021

(87) PCT Pub. No.: WO2020/069054
PCT Pub. Date: Apr. 2, 2020

(65) Prior Publication Data
US 2021/0163544 A1    Jun. 3, 2021

Related U.S. Application Data

(60) Provisional application No. 62/737,190, filed on Sep. 27, 2018.

(51) Int. Cl.
*C07K 14/005* (2006.01)
*C12N 7/00* (2006.01)
*C12N 15/86* (2006.01)
*A61K 39/00* (2006.01)

(52) U.S. Cl.
CPC .............. *C07K 14/005* (2013.01); *C12N 7/00* (2013.01); *C12N 15/86* (2013.01); *A61K 39/00* (2013.01); *C12N 2740/15043* (2013.01); *C12N 2770/36122* (2013.01); *C12N 2770/36123* (2013.01); *C12N 2770/36134* (2013.01)

(58) Field of Classification Search
None
See application file for complete search history.

(56) References Cited

U.S. PATENT DOCUMENTS 9,353,353 B2 *   5/2016   Nabel ..................... C12N 7/00
2015/0111197 A1   4/2015   Despres et al.

FOREIGN PATENT DOCUMENTS

WO    2018020271 A1    2/2018

OTHER PUBLICATIONS

Sahadeo et al., PLoS Negl Trop Dis, 2015, 9(11):e0004199, 18 pages. (Year: 2015).*
GenBank Accession No. ALP46607.1, Nov. 2015. (Year: 2015).*
International Search Report [ISA/US] PCT/US2019/053049 dated Jan. 28, 2020.

* cited by examiner

*Primary Examiner* — Stacy B Chen
(74) *Attorney, Agent, or Firm* — Edwin S. Flores; Daniel J. Chalker; Chalker Flores, LLP

(57) ABSTRACT

The present invention includes nucleic acids, proteins, Chikungunya virus (CHIKV) Virus Like Particles (VLP), and methods of making a Chikungunya virus (CHIKV) Virus Like Particles (VLP) comprising: inserting one or more nucleic acids into a lentiviral backbone, wherein the nucleic acid encodes one or more Chikungunya virus (CHIKV) proteins; transfecting the one or more nucleic acids into the lentiviral backbone into a cell line; culturing the transfected cell line under conditions in which the Chikungunya virus (CHIKV) Virus Like Particles (VLP) are released from the cell line; and isolating the Chikungunya virus (CHIKV) Virus Like Particles (VLP) from a culture supernatant.

13 Claims, 3 Drawing Sheets
Specification includes a Sequence Listing.

SEQUENCE LISTING

```
<160> NUMBER OF SEQ ID NOS: 2

<210> SEQ ID NO 1
<211> LENGTH: 1248
<212> TYPE: PRT
<213> ORGANISM: Chikungunya virus

<400> SEQUENCE: 1

Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Lys Ala Gly Gln Leu Ala Gln Leu Ile Ser Ala Val
        35                  40                  45

Asn Lys Leu Thr Met Arg Val Val Pro Gln Gln Lys Pro Arg Lys Asn
    50                  55                  60

Arg Lys Asn Lys Lys Gln Lys Gln Lys Gln Gln Ala Pro Arg Asn Asn
65                  70                  75                  80

Thr Asn Gln Lys Lys Gln Pro Pro Lys Lys Lys Pro Val Gln Lys Lys
                85                  90                  95

Lys Lys Pro Gly Arg Arg Glu Arg Met Cys Met Lys Ile Glu Asn Asp
                100                 105                 110

Cys Ile Phe Glu Val Lys His Glu Gly Lys Val Thr Gly Tyr Ala Cys
            115                 120                 125
```

-continued

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
            165                 170                 175

Lys Phe Thr His Glu Lys Pro Glu Gly Tyr Tyr Asn Trp His His Gly
        180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Arg Pro Pro Cys Thr Pro Cys Cys Tyr
        275                 280                 285

Glu Lys Glu Pro Glu Lys Thr Leu Arg Met Leu Glu Asp Asn Val Met
    290                 295                 300

Ser Pro Gly Tyr Tyr Gln Leu Leu Gln Ala Ser Leu Thr Cys Ser Pro
305                 310                 315                 320

Arg Arg Gln Arg Arg Ser Ile Lys Asp His Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Gly Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Arg Glu Leu Pro Cys Ser Thr
465                 470                 475                 480

Tyr Ala Gln Ser Thr Ala Ala Thr Ala Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Ser Gln Thr Val Arg Tyr Lys Cys Asn Cys
        515                 520                 525

Gly Asp Ser Ser Glu Gly Leu Thr Thr Thr Asp Lys Val Ile Asn Asn
    530                 535                 540

```
Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Phe Gly Asp Arg
            565                 570                 575

Lys Gly Lys Val His Ile Pro Phe Pro Leu Ala Asn Val Thr Cys Arg
        580                 585                 590

Val Pro Lys Ala Arg Asn Pro Thr Val Thr Tyr Gly Lys Asn Gln Val
    595                 600                 605

Ile Met Leu Leu Tyr Pro Asp His Pro Thr Leu Leu Ser Tyr Arg Asn
610                 615                 620

Met Gly Glu Glu Pro Asn Tyr Gln Gly Glu Trp Val Thr His Lys Lys
625                 630                 635                 640

Glu Ile Arg Leu Thr Val Pro Thr Gly Leu Glu Val Thr Trp Gly
            645                 650                 655

Asn Asn Glu Pro Tyr Lys Tyr Trp Pro Gln Leu Ser Thr Asn Gly Thr
                660                 665                 670

Ala His Gly His Pro His Glu Ile Ile Leu Tyr Tyr Glu Leu Tyr
            675                 680                 685

Pro Thr Met Thr Ala Val Val Leu Ser Val Ala Ser Phe Ile Leu Leu
690                 695                 700

Ser Met Val Gly Val Ala Val Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Val Tyr Leu Trp Asn Glu Gln Gln Pro Leu Phe Trp Met
            755                 760                 765

Gln Ala Leu Ile Pro Leu Ala Ala Leu Ile Val Leu Cys Asn Cys Leu
            770                 775                 780

Arg Leu Leu Pro Cys Cys Cys Lys Met Leu Thr Phe Leu Ala Val Leu
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
850                 855                 860

Pro Ser Pro Tyr Val Lys Cys Cys Gly Thr Ala Glu Cys Lys Asp Lys
865                 870                 875                 880

Ser Leu Pro Asp Tyr Ser Cys Lys Val Phe Thr Gly Val Tyr Pro Phe
            885                 890                 895

Met Trp Gly Gly Ala Tyr Cys Phe Cys Asp Thr Glu Asn Thr Gln Leu
                900                 905                 910

Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
            930                 935                 940

Leu Tyr Gln Gly Asn Asn Ile Thr Val Ala Ala Tyr Ala Asn Gly Asp
945                 950                 955                 960
```

-continued

His Ala Val Thr Val Lys Asp Ala Lys Phe Ile Val Gly Pro Met Ser
            965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
            995                1000                1005

Phe Gly Asp Ile Gln Ser Arg Thr Pro Glu Ser Glu Asp Val Tyr
       1010                1015                1020

Ala Asn Thr Gln Leu Val Leu Gln Arg Pro Ser Ala Gly Thr Val
       1025                1030                1035

His Val Pro Tyr Ser Gln Ala Pro Ser Gly Phe Lys Tyr Trp Leu
       1040                1045                1050

Lys Glu Arg Gly Ala Ser Leu Gln His Thr Ala Pro Phe Gly Cys
       1055                1060                1065

Gln Ile Ala Thr Asn Pro Val Arg Ala Met Asn Cys Ala Val Gly
       1070                1075                1080

Asn Met Pro Ile Ser Ile Asp Ile Pro Asp Ala Ala Phe Thr Arg
       1085                1090                1095

Val Val Asp Ala Pro Ser Leu Thr Asp Met Ser Cys Glu Val Ser
       1100                1105                1110

Ala Cys Thr His Ser Ser Asp Phe Gly Gly Val Ala Ile Ile Lys
       1115                1120                1125

Tyr Ala Ala Ser Lys Lys Gly Lys Cys Ala Val His Ser Met Thr
       1130                1135                1140

Asn Ala Val Thr Ile Arg Glu Ala Glu Ile Glu Val Glu Gly Asn
       1145                1150                1155

Ser Gln Leu Gln Ile Ser Phe Ser Thr Ala Leu Ala Ser Ala Glu
       1160                1165                1170

Phe Arg Val Gln Val Cys Ser Thr Gln Val His Cys Ala Ala Glu
       1175                1180                1185

Cys His Pro Pro Lys Asp His Ile Val Asn Tyr Pro Ala Ser His
       1190                1195                1200

Thr Thr Leu Gly Val Gln Asp Ile Ser Ala Thr Ala Met Ser Trp
       1205                1210                1215

Val Gln Lys Ile Thr Gly Gly Val Gly Leu Val Val Ala Val Ala
       1220                1225                1230

Ala Leu Ile Leu Ile Val Val Leu Cys Val Ser Phe Ser Arg His
       1235                1240                1245

<210> SEQ ID NO 2
<211> LENGTH: 3744
<212> TYPE: DNA
<213> ORGANISM: Chikungunya virus

<400> SEQUENCE: 2
atggagttca tccccacaca dacccttttat aaccggagat accagcccag gccttggacc      60
ccacgcccaa caatccaggt catcaggcct cggccaagac acagaggaa ggcaggacag       120 ctggcacagc tgatcagcgc cgtgaataag ctgaccatgc gcgtggtgcc ccagcagaag      180
cctcggaaga acagaaagaa taagaagcag aagcagaagc agcaggcccc aaggaacaat      240
accaaccaga gaagcagcc ccccaagaag aagcctgtgc agaagaagaa gaagccaggc      300
aggcgcgagc gcatgtgcat gaagatcgag aatgattgca tcttcgaggt gaagcacgag      360
ggcaaggtga ccggctacgc ctgtctggtg ggcgacaaag tgatgaagcc cgcccacgtg      420

-continued

```
aagggcacaa tcgacaacgc cgatctggcc aagctggcct tcaagaggag ctccaagtat    480
gatctggagt gcgcccagat ccccgtgcac atgaagagcg acgcctccaa gtttacccac    540
gagaagcctg agggctacta taattggcac cacggagcag tgcagtactc tggaggcagg    600
ttcaccatcc ctacaggagc aggcaagcca ggcgacagcg gcagacccat ctttgataat    660
aagggaagag tggtggcaat cgtgctggga ggagcaaacg agggcgccag aaccgccctg    720
agcgtggtga catggaataa ggatatcgtg accaagatca cacctgaggg agcagaggag    780
tggtctctgg caatcccagt gatgtgcctg ctggccaaca ccacattccc atgtagccgg    840
ccaccatgca ccccatgctg ttacgagaaa gagcctgaga agacactgag aatgctggag    900
gacaatgtga tgtcccctgg ctactatcag ctgctgcagg cctctctgac ctgtagccca    960
cggagacaga ggcgctctat caaggatcac tttaacgtgt ataaggccac aaggccttac   1020
ctggcacact gtccagactg cggagaggga cactcttgcc acagcccagt ggccctggag   1080
cggatcagaa atgaggccac cgatggcaca ctgaagatcc aggtgagcct gcagatcggc   1140
atcaagaccg acgattccca cgactggaca aagctgcgct acatggacaa ccacatgcca   1200
gccgatgcag agagggcagg actgttcgtg agaaccagcg cccctgtac aatcaccggc    1260 acaatgggcc acttcatcct ggcaaggtgc ccaaggggag agaccctgac agtgggcttt   1320
accgatggcc gcaagatctc tcacagctgt acacacctt tccaccacga ccctccagtg    1380 atcgccgcg agaagtttca ctcccggcca cagcacggaa gagagctgcc ctgctctacc    1440
tatgcacaga gcaccgccgc cacagccgag gagatcgagg tgcacatgcc ccctgacacc   1500
cccgatcgga cactgatgtc ccagcagtct ggcaacgtga agatcaccgt gaatagccag   1560
acagtgagat acaagtgtaa ctgcggcgac tctagcgagg gcctgaccac aaccgataaa   1620
gtgatcaaca attgtaaggt ggaccagtgc cacgccgccg tgaccaacca caagaagtgg   1680
cagtataatt ccccactggt gcccaggaac gccgagttcg gcgatcgcaa gggcaaggtg   1740
cacatccctt ttccactggc caatgtgacc tgcagggtgc ctaaggcccg caatccaacc   1800
gtgacatacg gcaagaacca ggtcatcatg ctgctgtatc ctgaccaccc aacactgctg   1860
agctacagga acatgggcga ggagcctaat tatcaggagg agtgggtgac ccacaagaag   1920
gagatccgcc tgaccgtgcc aacagagggc ctggaggtga catgggcaa caatgagccc   1980 tataagtact ggcctcagct gtccaccaac ggaacagcac acggacaccc acacgagatc   2040
atcctgtact attacgagct gtaccctacc atgacagccg tggtgctgag cgtggcctcc   2100
ttcatcctgc tgtccatggt gggagtggca gtgggaatgt gcatgtgcgc acggagaagg   2160
tgcatcaccc catatgagct gacccccggc gccacagtgc cttttctgct gtctctgatc   2220
tgctgtatcc ggaccgccaa ggccgccaca tatcaggagg ccgccgtgta cctgtggaac   2280
gagcagcagc ccctgttctg gatgcaggcc ctgatccctc tggccgccct gatcgtgctg   2340
tgcaattgcc tgagactgct gccttgctgt gcaagatgc tgacctttct ggccgtgctg   2400
tccgtgggcg cccacacagt gtctgcctac gagcacgtga ccgtgatccc caatacagtg   2460
ggcgtgcctt acaagaccct ggtgaaccgg ccaggctatt ctcccatggt gctggagatg   2520
gagctgctga gcgtgaccct ggagccaaca ctgtccctgg attatatcac ctgtgagtac   2580
aagacagtga tccccagccc ttacgtgaag tgttgcggca ccgccgagtg taaggacaag   2640
tccctgccag attattcttg caaggtgttc acaggcgtgt atcctttat gtggggcggc   2700 gcctactgtt tctgcgacac cgagaacaca cagctgtccg aggcccacgt ggagaagtcc   2760
gagtcttgca agaccgagtt tgcctctgcc tacagagccc acacagcaag cgcctccgcc   2820
```

```
aagctgagag tgctgtacca gggcaacaat atcaccgtgg ccgcctatgc caatggcgac    2880
cacgccgtga cagtgaagga tgccaagttc atcgtgggac ccatgtcctc tgcctggacc    2940
ccatttgaca ataagatcgt ggtgtacaag ggcgacgtgt ataacatgga ttacccaccc    3000
ttcggcgcag gcaggcctgg acagtttggc gatatccaga gccgcacccc agagtccgag    3060
gacgtgtatg ccaacacaca gctggtgctg cagaggccaa gcgccggcac cgtgcacgtg    3120
ccatactccc aggcccccte tggcttcaag tattggctga aggagagggg agcatccctg    3180
cagcacaccg caccatttgg ctgtcagatc gccacaaatc ccgtgagagc catgaactgc    3240
gccgtgggca atatgccaat cagcatcgac atccccgatg ccgccttcac cagagtggtg    3300
gacgcccctt ccctgacaga tatgagctgt gaggtgtccg cctgcaccca cagctccgac    3360
tttggcggcg tggccatcat caagtacgcc gcctctaaga agggcaagtg tgccgtgcac    3420
agcatgacca acgccgtgac aatccgggag gccgagatcg aggtggaggg caatagccag    3480
ctgcagatct ctttcagcac cgccctggcc tccgccgagt ttagagtgca ggtgtgctct    3540
acacaggtgc actgtgccgc cgagtgccac cctccaaagg atcacatcgt gaactatcca    3600
gcatcccaca caaccctggg agtgcaggac atctctgcca ccgccatgag ctgggtgcag    3660
aagatcacag gaggagtggg actggtggtg gcagtggccg ccctgatcct gatcgtggtg    3720
ctgtgcgtgt ccttctctag acac                                           3744
```

STABLE CELL LINE SECRETING CHIKUNGUNYA VIRUS (CHIKV) VIRUS LIKE PARTICLES (VLP) FOR VACCINES

CROSS-REFERENCE TO RELATED APPLICATIONS

This application is the National Stage of International Application No. PCT/US2019/053049, filed on Sep. 26, 2019 claiming priority to U.S. Provisional Application Ser. No. 62/737,190, filed Sep. 27, 2018, the contents of each of which are incorporated by reference herein.

STATEMENT OF FEDERALLY FUNDED RESEARCH

Not applicable.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Sep. 25, 2019, is named TECH2130WO_SeqList.txt and is 16, kilo bytes in size.

TECHNICAL FIELD OF THE INVENTION

The present invention relates in general to the field of stable cell line secreting Chikungunya Virus (CHIKV) Virus Like Particles (VLP) for use as vaccines.

BACKGROUND OF THE INVENTION

Without limiting the scope of the invention, its background is described in connection with Chikungunya Virus (CHIKV) Virus Like Particles (VLP).

Chikungunya is a viral disease caused by Chikungunya virus (CHIKV) and transmitted to humans by infected mosquitoes. The symptoms of Chikungunya include fever and joint pain. Other symptoms include headache, nausea, muscle pain, fatigue and rash. According to the World Health Organization (WHO) website, cince 2005, India, Indonesia, Maldives, Myanmar and Thailand have reported over 1.9 million cases.

Currently, there is no specific treatment or vaccine for CHIKV. Virus Like Particles (VLP) provides a safe, economical and effective vaccine platform for many viral diseases. The success of the VLP vaccine against Papilloma virus (HPV) exemplifies the success of this platform. Currently there are no VLP vaccines against CHIKV approved for human use.

One example of a VLP vaccine for CHIKV developed by the National Institutes of Health (NIH) relies on generating VLPs by transfecting 293T cells and collecting VLPs in the supernatant. This requires repeated transfection of cells making the platform expensive for use in developing countries where this problem persists.

SUMMARY OF THE INVENTION

In one embodiment, the present invention includes a nucleic acid encoding a consensus Chikungunya virus (CHIKV) nucleic acid sequence comprising the nucleic acid of SEQ ID NO:2. In one aspect, the nucleic acid is inserted into the lentiviral vector. In another aspect, the nucleic acid expresses one or more proteins of SEQ ID NO:1. In another aspect, the nucleic acid is transfected into a cell line. In another aspect, the nucleic acid is transfected into a human cell line. In another aspect, the nucleic acid is transfected into a 293T cell line. In another aspect, the nucleic acid is stably transfected in a cell line.

In another embodiment, the present invention includes a method of making a Chikungunya virus (CHIKV) Virus Like Particles (VLP) comprising: inserting one or more nucleic acids into a lentiviral backbone, wherein the nucleic acid encodes one or more Chikungunya virus (CHIKV) proteins; transfecting the one or more nucleic acids into the lentiviral backbone into a cell line; culturing the transfected cell line under conditions in which the Chikungunya virus (CHIKV) Virus Like Particles (VLP) are released from the cell line; and isolating the Chikungunya virus (CHIKV) Virus Like Particles (VLP) from a culture supernatant. In one aspect, the nucleic acid expresses one or more proteins of SEQ ID NO:1. In another aspect, the nucleic acid is transfected into a cell line. In another aspect, the nucleic acid is transfected into a human cell line. In another aspect, the nucleic acid is transfected into a 293T cell line. In another aspect, the nucleic acid is stably transfected in a cell line.

In another embodiment, the present invention includes a vaccine comprising an isolated and purified Chikungunya virus (CHIKV) Virus Like Particles (VLP) that comprises at least one CHIKV structural protein.

In another embodiment, the present invention includes a cell line transformed with a nucleic acid vector comprising a nucleic acid sequence that encodes comprising a lentiviral backbone and one or more Chikungunya virus (CHIKV) proteins. In one aspect, the one or more Chikungunya virus (CHIKV) proteins are expressed by a nucleic acid sequence codon optimized for expression in human cells. In another aspect, the one or more Chikungunya virus (CHIKV) proteins are expressed by a nucleic acid sequence codon optimized for expression in human cells of SEQ ID NO:2. In another aspect, the one or more Chikungunya virus (CHIKV) proteins have the amino acid sequence of SEQ ID NO:1. In another aspect, the cell line is stably transfected with the nucleic acid vector.

In another embodiment, the present invention includes a purified Chikungunya virus (CHIKV) Virus Like Particles (VLP) comprising the amino acid sequence of SEQ ID NO:1. In another aspect, the CHIKV VLP are produced in a stably transformed cell line. In another aspect, the CHIKV VLP are produced in a stably transformed human cell line. In another aspect, the CHIKV VLP are produced in a stably transformed 293T cell line. In another aspect, the CHIKV VLP are isolated from at least one of: a culture supernatant, or the cell lines.

BRIEF DESCRIPTION OF THE DRAWINGS

For a more complete understanding of the features and advantages of the present invention, reference is now made to the detailed description of the invention along with the accompanying figures and in which:

In FIG. 2A, the CHKV structural proteins were cloned into the lentiviral vector pLenti6/5-D-Topo and used to produce lentiviral particles containing the CHKV-E1/E2. 293T cells were then transduced with the above lentiviral particles and cells selected by culturing in the presence of blasticidin. Bulk selected cells were confirmed for E1/E2 protein expression via western blotting. Subsequently, cells were plated in 96 well plates using limiting dilution and clones arising from single viable cells selected. In FIG. 2B, the culture supernatants were harvested from 293T single cell clones and concentrated by ultracentrifugation. Expression of the E1/E2 proteins in the supernatants was determined by western blotting.

DETAILED DESCRIPTION OF THE INVENTION

Figure 1A:
FIG. 1A is a schematic of a lentiviral expression vector with CHKV structural proteins for production of capsid containing virus like particles.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention includes a CHKV vaccine candidate that forms Virus Like Particles (VLPs) in a cell line that stably produces the CHKV VLPs. The CHKV virus genome was cleaved to express the capsid (C), pre-membrane (PrM), envelope (E), and other non-structural proteins, none of which are capable of generating host infections, but are still able to elicit an immune response. These CHKV VLPs were then coupled with the backbone of a West Nile virus (WNV) reporter gene, to generate reporter virus-like particles, which can be detected by luciferase assays, and when used as a vaccine, were able to trigger the production of a robust immune response in animals. The antibodies elicited were further shown to be neutralizing antibodies against CHKV vaccine.

As used throughout the present specification the following abbreviations are used: TF, transcription factor; ORF, open reading frame; kb, kilobase (pairs); UTR, untranslated region; kD, kilodalton; PCR, polymerase chain reaction; RT, reverse transcriptase.

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer DNA segment(s) from one cell to another. The vector may be further defined as one designed to propagate Chikungunya Virus (CHIKV) Virus Like Particle sequences, or as an expression vector that includes a promoter operatively linked to the Chikungunya Virus (CHIKV) Virus Like Particle sequence, or one designed to cause such a promoter to be introduced. The vector may exist in a state independent of the host cell chromosome, or may be integrated into the host cell chromosome.

The term "host cell" refers to cells that have been engineered to contain nucleic acid segment that encodes a Chikungunya Virus (CHIKV) Virus Like Particle, or altered segments, whether archeal, prokaryotic, or eukaryotic. Thus, engineered, or recombinant cells, are distinguishable from naturally occurring cells that do not contain recombinantly introduced genes through the hand of man.

As used herein, the terms "polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "isolated" refers to materials, such as nucleic acid molecules and/or proteins that are substantially free or otherwise removed from components that normally accompany or interact with the materials in a naturally occurring environment.

The Chikungunya Virus (CHIKV) Virus Like Particles variants of the present invention may contain alterations in the coding regions, non-coding regions, or both. Polynucleotide variants can be produced for a variety of reasons, e.g., to optimize codon expression for a particular host (change codons in the human mRNA to those preferred by a bacterial host such as *E. coli*), as is the case in certain embodiments of the present invention and which are known to those of skill in the art following, e.g., Sambrook and Russell, Molecular Cloning 3rd Ed. Cold Spring Harbor Laboratory Press, Cold Spring Harbor N.Y. 5 (2001) and by Ausubel et al., Current Protocols In Molecular Biology, John Wiley and Sons, Inc. (1998), and updates thereof.

Stable cell line secreting Chikungunya Virus (CHIKV) Virus Like Particles for vaccine use. Chikungunya is a viral disease caused by Chikungunya virus (CHIKV) and transmitted to humans by infected mosquitoes. Symptoms of Chikungunya include fever and joint pain. Other symptoms include headache, nausea, muscle pain, fatigue and rash. Since 2005, India, Indonesia, Maldives, Myanmar and Thailand have reported over 1.9 million cases (WHO website).

Currently there is no specific treatment or vaccine for CHIKV. Virus Like Particles (VLP) provide a safe, economical and effective vaccine platform for many viral diseases. The success of the VLP vaccine against Papilloma virus (HPV) exemplifies the success of this platform.

Currently there are no VLP vaccines against CHIKV approved for human use. A VLP vaccine for CHIKV developed by NIH relies on generating VLPs by transfecting 293T cells and collecting VLPs in the supernatant. This requires repeated transfection of cells making the platform expensive for use in developing countries where this problem persists.

The present inventors have developed a VLP platform for the related arbovirus, Zika virus, using stable cell lines that constitutively secrete VLPs and demonstrated that this platform can provide an economical, safe and highly effective vaccine especially for use in humans. A similar stable cell line method was used to generate CHIKV VLP secreting cell line. The present invention provides three substantial improvements and advantages over the prior art.

1. The inventors generated a consensus sequence of 478 CHIKV sequences from year 2006 onwards to represent the most current CHIKV isolates. The artificial consensus sequence and translation was codon optimized to drive high expression of the proteins. The use of the consensus sequence provides a vaccine that is most relevant to current outbreaks.

2. The inventors used a lentiviral system to generate stable cell lines that constitutively express CHIKV structural proteins and secrete the VLPs in the supernatant.

3. Finally, the inventors optimized production and purification of the VLPs from these stable cell lines.

Chikungunya Virus Consensus Sequences used in the vaccine:

```
Amino acid sequence: SEQ ID NO: 1.
MEFIPTQTFYNRRYQPRPWTPRPTIQVIRPRPRPQRKAGQLAQLISAVNKLTMRV

VPQQKPRKNRKNKKQKQKQQAPRNNTNQKKQPPKKKPVQKKKKPGRRERMCMKIEN

DCIFEVKHEGKVTGYACLVGDKVMKPAHVKGTIDNADLAKLAFKRSSKYDLECAQIPV

HMKSDASKFTHEKPEGYYNWHHGAVQYSGGRFTIPTGAGKPGDSGRPIFDNKGRVVAI

VLGGANEGARTALSVVTWNKDIVTKITPEGAEEWSLAIPVMCLLANTTFPCSRPPCTPC

CYEKEPEKTLRMLEDNVMSPGYYQLLQASLTCSPRRQRRSIKDHFNVYKATRPYLAHC

PDCGEGHSCHSPVALERIRNEATDGTLKIQVSLQIGIKTDDSHDWTKLRYMDNHMPAD

AERAGLFVRTSAPCTITGTMGHFILARCPKGETLTVGFTDGRKISHSCTHPFHHDPPVIGR

EKFHSRPQHGRELPCSTYAQSTAATAEEIEVHMPPDTPDRTLMSQQSGNVKITVNSQTV

RYKCNCGDSSEGLTTTDKVINNCKVDQCHAAVTNHKKWQYNSPLVPRNAEFGDRKGK

VHIPFPLANVTCRVPKARNPTVTYGKNQVIMLLYPDHPTLLSYRNMGEEPNYQEEWVT

HKKEIRLTVPTEGLEVTWGNNEPYKYWPQLSTNGTAHGHPHEIILYYYELYPTMTAVV

LSVASFILLSMVGVAVGMCMCARRRCITPYELTPGATVPFLLSLICCIRTAKAATYQEAA

VYLWNEQQPLFWMQALIPLAALIVLCNCLRLLPCCCKMLTFLAVLSVGAHTVSAYEHV

TVIPNTVGVPYKTLVNRPGYSPMVLEMELLSVTLEPTLSLDYITCEYKTVIPSPYVKCCG

TAECKDKSLPDYSCKVFTGVYPFMWGGAYCFCDTENTQLSEAHVEKSESCKTEFASAY

RAHTASASAKLRVLYQGNNITVAAYANGDHAVTVKDAKFIVGPMSSAWTPFDNKIVV

YKGDVYNMDYPPFGAGRPGQFGDIQSRTPESEDVYANTQLVLQRPSAGTVHVPYSQAP

SGFKYWLKERGASLQHTAPFGCQIATNPVRAMNCAVGNMPISIDIPDAAFTRVVDAPSL

TDMSCEVSACTHSSDFGGVAIIKYAASKKGKCAVHSMTNAVTIREAEIEVEGNSQLQISF

STALASAEFRVQVCSTQVHCAAECHPPKDHIVNYPASHTTLGVQDISATAMSWVQKITG

GVGLVVAVAALILIVVLCVSFSRH

DNA sequence SEQ ID NO: 2
ATGGAGTTCATCCCCACACAGACCTTTTATAACCGGAGATACCAGCCCAGGC

CTTGGACCCCACGCCCAACAATCCAGGTCATCAGGCCTCGGCCAAGACCACAGAGG

AAGGCAGGACAGCTGGCACAGCTGATCAGCGCCGTGAATAAGCTGACCATGCGCGT

GGTGCCCCAGCAGAAGCCTCGGAAGAACAGAAAGAATAAGAAGCAGAAGCAGAAG

CAGCAGGCCCCAAGGAACAATACCAACCAGAAGAAGCAGCCCCCCAAGAAGAAGC

CTGTGCAGAAGAAGAAGAAGCCAGGCAGGCGCGAGCGCATGTGCATGAAGATCGA

GAATGATTGCATCTTCGAGGTGAAGCACGAGGGCAAGGTGACCGGCTACGCCTGTC
```

-continued

```
TGGTGGGCGACAAAGTGATGAAGCCCGCCCACGTGAAGGGCACAATCGACAACGC
CGATCTGGCCAAGCTGGCCTTCAAGAGGAGCTCCAAGTATGATCTGGAGTGCGCCC
AGATCCCCGTGCACATGAAGAGCGACGCCTCCAAGTTTACCCACGAGAAGCCTGAG
GGCTACTATAATTGGCACCACGGAGCAGTGCAGTACTCTGGAGGCAGGTTCACCAT
CCCTACAGGAGCAGGCAAGCCAGGCGACAGCGGCAGACCCATCTTTGATAATAAGG
GAAGAGTGGTGGCAATCGTGCTGGGAGGAGCAAACGAGGGCGCCAGAACCGCCCT
GAGCGTGGTGACATGGAATAAGGATATCGTGACCAAGATCACACCTGAGGGAGCA
GAGGAGTGGTCTCTGGCAATCCCAGTGATGTGCCTGCTGGCCAACACCACATTCCCA
TGTAGCCGGCCACCATGCACCCCATGCTGTTACGAGAAAGAGCCTGAGAAGACACT
GAGAATGCTGGAGGACAATGTGATGTCCCCTGGCTACTATCAGCTGCTGCAGGCCT
CTCTGACCTGTAGCCCACGGAGACAGAGGCGCTCTATCAAGGATCACTTTAACGTGT
ATAAGGCCACAAGGCCTTACCTGGCACACTGTCCAGACTGCGGAGAGGGACACTCT
TGCCACAGCCCAGTGGCCCTGGAGCGGATCAGAAATGAGGCCACCGATGGCACACT
GAAGATCCAGGTGAGCCTGCAGATCGGCATCAAGACCGACGATTCCCACGACTGGA
CAAAGCTGCGCTACATGGACAACCACATGCCAGCCGATGCAGAGAGGGCAGGACT
GTTCGTGAGAACCAGCGCCCCCTGTACAATCACCGGCACAATGGGCCACTTCATCCT
GGCAAGGTGCCCAAAGGGAGAGACCCTGACAGTGGGCTTTACCGATGGCCGCAAG
ATCTCTCACAGCTGTACACACCCTTTCCACCACGACCCTCCAGTGATCGGCCGCGAG
AAGTTTCACTCCCGGCCACAGCACGGAAGAGAGCTGCCCTGCTCTACCTATGCACA
GAGCACCGCCGCCACAGCCGAGGAGATCGAGGTGCACATGCCCCCTGACACCCCCG
ATCGGACACTGATGTCCCAGCAGTCTGGCAACGTGAAGATCACCGTGAATAGCCAG
ACAGTGAGATACAAGTGTAACTGCGGCGACTCTAGCGAGGGCCTGACCACAACCGA
TAAAGTGATCAACAATTGTAAGGTGGACCAGTGCCACGCCGCCGTGACCAACCACA
AGAAGTGGCAGTATAATTCCCCACTGGTGCCCAGGAACGCCGAGTTCGGCGATCGC
AAGGGCAAGGTGCACATCCCTTTTCCACTGGCCAATGTGACCTGCAGGGTGCCTAA
GGCCCGCAATCCAACCGTGACATACGGCAAGAACCAGGTCATCATGCTGCTGTATC
CTGACCACCCAACACTGCTGAGCTACAGGAACATGGGCGAGGAGCCTAATTATCAG
GAGGAGTGGGTGACCCACAAGAAGGAGATCCGCCTGACCGTGCCAACAGAGGGCC
TGGAGGTGACATGGGGCAACAATGAGCCCTATAAGTACTGGCCTCAGCTGTCCACC
AACGGAACAGCACACGGACACCCACACGAGATCATCCTGTACTATTACGAGCTGTA
CCCTACCATGACAGCCGTGGTGCTGAGCGTGGCCTCCTTCATCCTGCTGTCCATGGT
GGGAGTGGCAGTGGGAATGTGCATGTGCGCACGGAGAAGGTGCATCACCCCATATG
AGCTGACCCCCGGCGCCACAGTGCCTTTTCTGCTGTCTCTGATCTGCTGTATCCGGA
CCGCCAAGGCCGCCACATATCAGGAGGCCGCCGTGTACCTGTGGAACGAGCAGCAG
CCCCTGTTCTGGATGCAGGCCCTGATCCCTCTGGCCGCCCTGATCGTGCTGTGCAAT
TGCCTGAGACTGCTGCCTTGCTGTTGCAAGATGCTGACCTTTCTGGCCGTGCTGTCC
GTGGGCGCCCACACAGTGTCTGCCTACGAGCACGTGACCGTGATCCCCAATACAGT
GGGCGTGCCTTACAAGACCCTGGTGAACCGGCCAGGCTATTCTCCCATGGTGCTGG
AGATGGAGCTGCTGAGCGTGACCCTGGAGCCAACACTGTCCCTGGATTATATCACCT
GTGAGTACAAGACAGTGATCCCCAGCCCTTACGTGAAGTGTTGCGGCACCGCCGAG
TGTAAGGACAAGTCCCTGCCAGATTATTCTTGCAAGGTGTTCACAGGCGTGTATCCC
```

-continued
```
TTTATGTGGGGCGGCGCCTACTGTTTCTGCGACACCGAGAACACACAGCTGTCCGAG

GCCCACGTGGAGAAGTCCGAGTCTTGCAAGACCGAGTTTGCCTCTGCCTACAGAGC

CCACACAGCAAGCGCCTCCGCCAAGCTGAGAGTGCTGTACCAGGGCAACAATATCA

CCGTGGCCGCCTATGCCAATGGCGACCACGCCGTGACAGTGAAGGATGCCAAGTTC

ATCGTGGGACCCATGTCCTCTGCCTGGACCCCATTTGACAATAAGATCGTGGTGTAC

AAGGGCGACGTGTATAACATGGATTACCCACCCTTCGGCGCAGGCAGGCCTGGACA

GTTTGGCGATATCCAGAGCCGCACCCCAGAGTCCGAGGACGTGTATGCCAACACAC

AGCTGGTGCTGCAGAGGCCAAGCGCCGGCACCGTGCACGTGCCATACTCCCAGGCC

CCCTCTGGCTTCAAGTATTGGCTGAAGGAGAGGGGAGCATCCCTGCAGCACACCGC

ACCATTTGGCTGTCAGATCGCCACAAATCCCGTGAGAGCCATGAACTGCGCCGTGG

GCAATATGCCAATCAGCATCGACATCCCCGATGCCGCCTTCACCAGAGTGGTGGAC

GCCCCTTCCCTGACAGATATGAGCTGTGAGGTGTCCGCCTGCACCCACAGCTCCGAC

TTTGGCGGCGTGGCCATCATCAAGTACGCCGCCTCTAAGAAGGGCAAGTGTGCCGT

GCACAGCATGACCAACGCCGTGACAATCCGGGAGGCCGAGATCGAGGTGGAGGGC

AATAGCCAGCTGCAGATCTCTTTCAGCACCGCCCTGGCCTCCGCCGAGTTTAGAGTG

CAGGTGTGCTCTACACAGGTGCACTGTGCCGCCGAGTGCCACCCTCCAAAGGATCA

CATCGTGAACTATCCAGCATCCCACACAACCCTGGGAGTGCAGGACATCTCTGCCA

CCGCCATGAGCTGGGTGCAGAAGATCACAGGAGGAGTGGGACTGGTGGTGGCAGT

GGCCGCCCTGATCCTGATCGTGGTGCTGTGCGTGTCCTTCTCTAGACAC
```

Figure 1B:
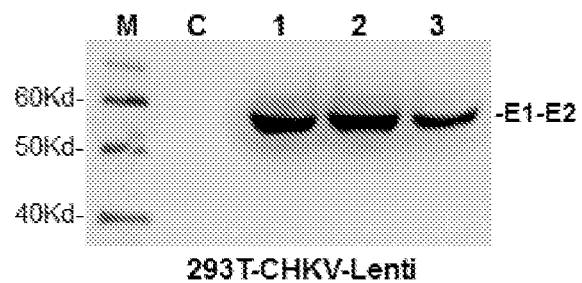
FIG. 1B is a Western Blot showing the culture supernatants harvested from 293T cells stably transfected and expressing the CHKV structural proteins (293T-CHKV-Lenti) and analyzed for CHKV E1-E2 protein expression. Lanes 1, 2 and 3 represent supernatants harvested from different days and C represents control supernatants from 293T cells. M-molecular weight markers.

FIG. 1A is a schematic of a lentiviral vector expression that includes CHKV structural proteins for production of capsid containing virus like particles. FIG. 1B is a Western Blot showing the culture supernatants harvested from 293T cells stably transfected and expressing the CHKV structural proteins (293T-CHKV-Lenti) and analyzed for CHKV E1-E2 protein expression. Lanes 1, 2 and 3 represent supernatants harvested from different days and C represents control supernatants from 293T cells. M-molecular weight markers.

Figure 2A:
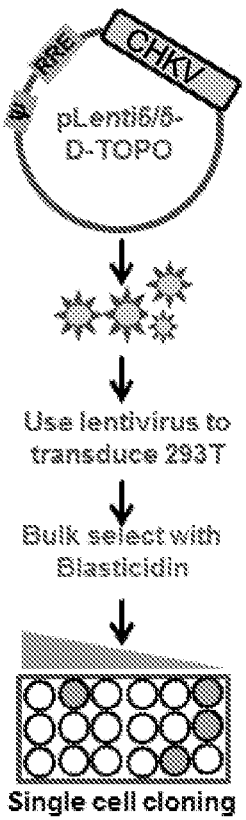
FIGS. 2A and 2B show the establishment of a single cell clones expressing CHKV Structural proteins.
Figure 2B:
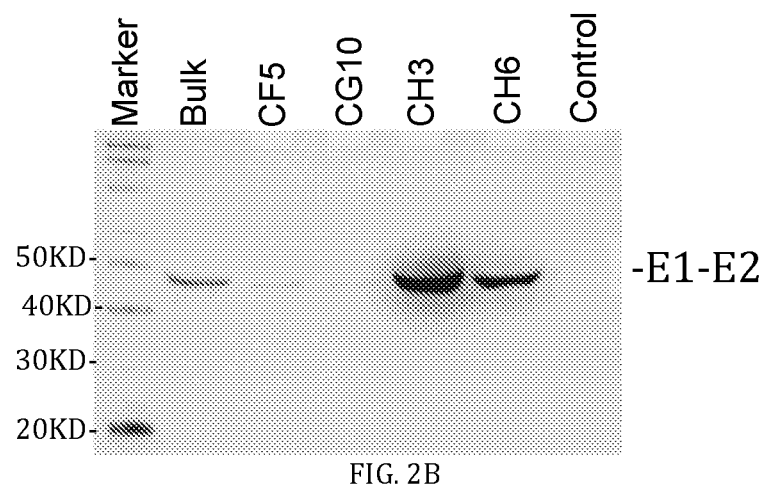

FIGS. 2A and 2B show the establishment of a single cell clones expressing CHKV Structural proteins. In FIG. 2A, the CHKV structural proteins were cloned into the lentiviral vector pLenti6/5-D-Topo and used to produce lentiviral particles containing the CHKV-E1/E2. 293T cells were then transduced with the above lentiviral particles and cells selected by culturing in the presence of blasticidin. Bulk selected cells were confirmed for E1/E2 protein expression via western blotting. Subsequently, cells were plated in 96 well plates using limiting dilution and clones arising from single viable cells selected. In FIG. 2B, the culture supernatants were harvested from 293T single cell clones and concentrated by ultracentrifugation. Expression of the E1/E2 proteins in the supernatants was determined by western blotting.

Figure 3:
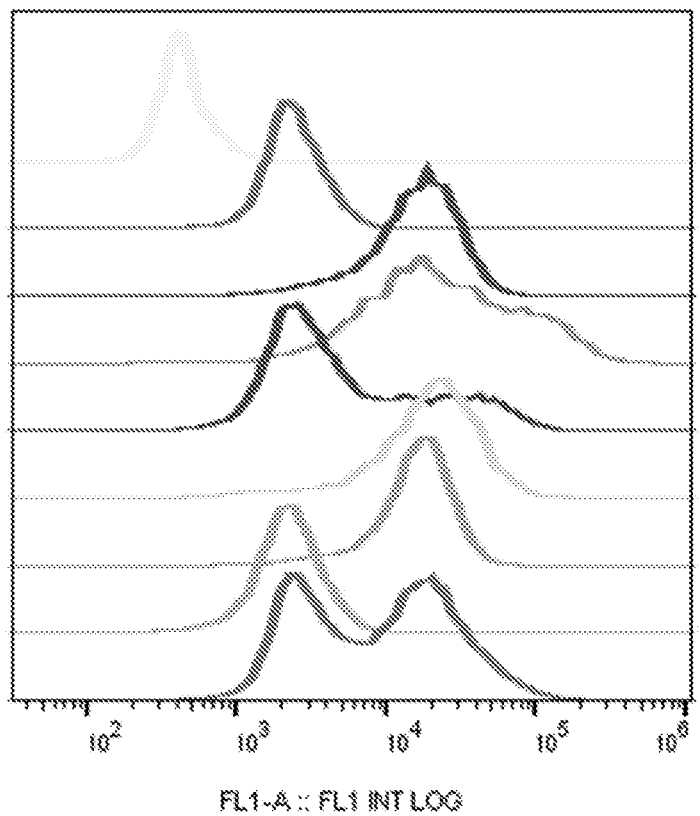
FIG. 3 is a flow cytometry analysis of single cell clones expressing the CHKV-E1/E2. Six different single cell clones of 293T cells expressing the CHKV-E1/E2 proteins were stained using the CHKV E protein antibody followed by flow cytometry analysis. The bulk selected cell line was used as control. The CH-6, CH-3 and CF-5 cell lines show good CHKV E protein expression. The flow cytometry is in the same order as the table below.

FIG. 3 is a flow cytometry analysis of single cell clones expressing the CHKV-E1/E2. Six different single cell clones of 293T cells expressing the CHKV-E1/E2 proteins were stained using the CHKV E protein antibody followed by flow cytometry analysis. The bulk selected cell line was used as control. The CH-6, CH-3 and CF-5 cell lines show good CHKV E protein expression. The flow cytometry is in the same order as the table below the graph.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (0, or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A nucleic acid comprising a consensus Chikungunya virus (CHIKV) nucleic acid sequence comprising SEQ ID NO: 2.

2. The nucleic acid of claim 1, wherein the nucleic acid is inserted in a lentiviral vector.

3. The nucleic acid of claim 1, wherein the nucleic acid is transfected in a cell line.

4. The nucleic acid of claim 1, wherein the nucleic acid is transfected in a human cell line.

5. The nucleic acid of claim 1, wherein the nucleic acid is transfected in a 293T cell line.

6. The nucleic acid of claim 1, wherein the nucleic acid is stably transfected in a cell line.

7. A method of making a Chikungunya virus (CHIKV) Virus Like Particles (VLP) comprising:
    inserting one or more nucleic acids comprising a consensus CHIKV nucleic acid comprising SEQ ID NO: 2 into a lentiviral backbone, wherein the nucleic acid encodes one or more CHIKV proteins of SEQ ID NO: 1;
    transfecting the lentiviral backbone into a cell line;
    culturing the transfected cell line under conditions in which the CHIKV VLPs are released from the cell line; and
    isolating the VLPs from a culture supernatant.

8. The method of claim 7, wherein the nucleic acid is transfected into a human cell line.

9. The method of claim 7, wherein the nucleic acid is transfected into a 293T cell line.

10. The method of claim 7, wherein the nucleic acid is stably transfected in a cell line.

11. A cell line transformed with a nucleic acid vector comprising a lentiviral backbone and a nucleic acid sequence that encodes one or more Chikungunya virus (CHIKV) proteins, wherein the one or more CHIKV proteins are expressed by a nucleic acid sequence codon optimized for expression in human cells comprising SEQ ID NO: 2.

12. The cell line of claim 11, wherein the one or more CHIKV proteins are from SEQ ID NO:1.

13. The cell line of claim 11, wherein the cell line is stably transfected with the nucleic acid vector.

\* \* \* \* \*